US010080650B2

(12) United States Patent
McCarthy

(10) Patent No.: US 10,080,650 B2
(45) Date of Patent: Sep. 25, 2018

(54) METHODS, DEVICES, AND SYSTEMS FOR TREATING PERICARDIAL TISSUE

(71) Applicant: BOSTON SCIENTIFIC SCIMED, INC., Maple Grove, MN (US)

(72) Inventor: Ray McCarthy, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 282 days.

(21) Appl. No.: 15/014,364

(22) Filed: Feb. 3, 2016

(65) Prior Publication Data

US 2016/0220362 A1 Aug. 4, 2016

Related U.S. Application Data

(60) Provisional application No. 62/111,373, filed on Feb. 3, 2015.

(51) Int. Cl.
| | |
|---|---|
| *G01N 1/00* | (2006.01) |
| *A61F 2/24* | (2006.01) |
| *C12N 5/077* | (2010.01) |
| *A01N 1/02* | (2006.01) |
| *A61L 27/36* | (2006.01) |

(52) U.S. Cl.
CPC .......... *A61F 2/2415* (2013.01); *A01N 1/0242* (2013.01); *A61L 27/3604* (2013.01); *A61L 27/367* (2013.01); *A61L 27/3625* (2013.01); *A61L 27/3645* (2013.01); *A61L 27/3687* (2013.01); *A61L 27/3691* (2013.01); *C12N 5/0657* (2013.01); *A61L 2430/20* (2013.01); *A61L 2430/40* (2013.01)

(58) Field of Classification Search
CPC ....................................................... G01N 1/00
See application file for complete search history.

(56) References Cited

U.S. PATENT DOCUMENTS

| | | | |
|---|---|---|---|
| 4,050,893 A | 9/1977 | Hancock et al. | |
| 5,855,602 A * | 1/1999 | Angell | A61F 2/2409 606/1 |
| 5,868,253 A * | 2/1999 | Krueger | A61F 2/0095 206/363 |
| 7,622,276 B2 | 11/2009 | Cunanan et al. | |
| 8,691,262 B2 | 4/2014 | Harris et al. | |
| 8,834,349 B2 | 9/2014 | Gregg et al. | |
| 2013/0012767 A1 | 1/2013 | Nguyen et al. | |

FOREIGN PATENT DOCUMENTS

| | | |
|---|---|---|
| WO | 1996007373 | 3/1996 |
| WO | 2012177941 | 12/2012 |
| WO | 2016126832 | 8/2016 |

OTHER PUBLICATIONS

Remi, Escande et al., "Pericardial Processing: Challenges, Outcomes and Future Prospects," Biomaterials Science and Engineering, Aug. 2011, Chapter 22, pp. 437-456 (20 pages).
"International Search Report and Written Opinion," for PCT Application No. PCT/US2016/016388, dated May 6, 2016 (11 pages).
"International Preliminary Report on Patentability," for PCT Application No. PCT/US2016/016388 dated Aug. 17, 2017 (8 pages).

* cited by examiner

*Primary Examiner* — Jyoti Nagpaul
(74) *Attorney, Agent, or Firm* — Pauly, DeVries Smith & Deffner LLC

(57) ABSTRACT

A method of treating pericardial tissue that includes contacting at least a portion of a pericardial sac with a chemical while the pericardial sac is tensioned by an application of fluid pressure to an inside face of the pericardial sac.

17 Claims, 9 Drawing Sheets

METHODS, DEVICES, AND SYSTEMS FOR TREATING PERICARDIAL TISSUE

This application claims the benefit of U.S. Provisional Application No. 62/111,373 filed Feb. 3, 2015, the contents of which are herein incorporated by reference.

FIELD

This document provides methods, devices, and systems for treating pericardial tissue. For example, pericardial tissue treated by methods, devices, and systems provided herein can be used in artificial heart valves.

BACKGROUND

Heart valve surgery can be used to repair or replace diseased heart valves. For example, heart valve replacement may be indicated when there is a narrowing of the native heart valve, commonly referred to as stenosis, or when the native valve leaks or regurgitates. The repair or replacement of diseased heart valves can include, for example, the introduction of a prosthetic heart valve that includes biological tissue heterologous to the patient (e.g., a heterograft or xenograft). Pericardial tissue from the sacs surrounding the hearts of animals, e.g. bovine, porcine, and equine, etc., are commonly used to create tissues that can be used in various medical applications. Biological tissue can have mechanical properties that vary within a single donor and/or from among several donors of the same species. For example, biological tissue from a single donor can have non-uniform thickness and/or stiffness, and the average thickness and/or stiffness of biological tissue can vary from one donor to another. The variation in mechanical properties of biological tissue used in replacement heart valves can impact the performance and/or durability of a replacement heart valve implanted in a patient. In some cases, the pericardial sacs can be cut, treated, and selected to obtain desirable mechanical properties, but these treatment and selection processes can result in significant quantities of unused pericardial tissue. Accordingly, there is a need improved techniques for treating and cutting pericardial tissue to obtain desirable properties while minimizing waste.

SUMMARY

Pericardial tissue treatment methods, devices, and systems provided herein can improve the mechanical properties of a pericardial sac to obtain desirable properties throughout the pericardial sac and/or increase the quantity of pericardial tissue suitable for use in a medical device. Methods, devices, and systems provided herein can chemically treat pericardial sacs to reduce the antigenicity of the xeno-tissue and/or to crosslink collagen fibers. Crosslinking the collagen fibers can increase the strength of the pericardial tissue. Methods, devices, and systems provided herein expose a pericardial sac to one or more chemical solutions while the pericardial sac can be tensioned by pressurizing the inside of the pericardial sac with fluid. An inside surface of the pericardial sac can be treated with a chemical solution while being pressurized using the chemical solution. An outside surface of the pericardial sac can be treated with a chemical solution while the inside of the pericardial sac is pressurized with a fluid. The inside and outside surfaces of the pericardial sac can be treated with different chemical solutions. The inside and outside surfaces of the pericardial sac can be treated while the pericardial sac is pressurized at different pressures. The pressure within that pericardial sac can be varied during exposure to a treating chemical solution.

In Example 1, a method of treating pericardial tissue includes contacting at least a portion of a pericardial sac with a chemical while the pericardial sac is tensioned by an application of fluid pressure to an inside face of the pericardial sac.

In Example 2, the method of Example 1, wherein the pericardial sac is tensioned by delivering the chemical to the inside face.

In Example 3, the method of Example 1 or Example 2, wherein the chemical is in an aqueous solution.

In Example 4, the method of one of Examples 1-3, wherein the chemical includes glutaraldehyde.

In Example 5, the method of one of Examples 1-4, further including securing a base of the pericardial sac to a rim of a pressurizing apparatus.

In Example 6, the method of Example 5, wherein the rim has a diameter within plus or minus 20% of the diameter of the base of the pericardial sac.

In Example 7, the method of Example 5 or Example 6, wherein the pressurizing apparatus includes at least one inlet or outlet adapted to supply at least one fluid to the inside face of the pericardial sac or evacuate a fluid from an outside face of the pericardial sac.

In Example 8, the method of one of Examples 5-7, wherein the pressurizing apparatus includes a vessel including a side wall and a bottom wall, the side wall including a vessel rim and a lid having a lid rim adapted to mate with the vessel rim to form an enclosure, wherein the base of the pericardial sac is secured between the vessel rim and the lid rim.

In Example 9, the method of one of Examples 1-8, wherein at least a portion of the pericardial sac is in contact with the chemical for at least 30 minutes.

In Example 10, the method of Example 9, wherein the fluid pressure applied to the inside face of the pericardial sac is varied during contact with the chemical.

In Example 11, the method of one of Examples 1-10, wherein the inside face is pressurized to a pressure of at least 0.4 atmospheres.

In Example 12, the method of one of Examples 1-11, wherein the inside face is treated with a first chemical solution and an outside face is treated with a second chemical solution that is different from the first chemical solution.

In Example 13, the method of one of Examples 1-12, wherein the inside face is treated with a chemical while the inside face is pressurized at a first pressure and an outside face is treated with a chemical while the inside face is pressurized at a second pressure that is different from the first pressure.

In Example 14, an apparatus for treating pericardial tissue includes a vessel and a lid. The vessel can include a side wall and a bottom wall, the side wall including a vessel rim. The lid can have a lid rim adapted to mate with the vessel rim to form an enclosure. The apparatus can be adapted to secure a base of a pericardial sac between the vessel rim and the lid rim and pressurize an inside face of the pericardial sac.

In Example 15, the apparatus of Example 14, further including a controller configured to supply fluids and chemicals to the vessel and the lid to treat a pericardial sac retained between the vessel rim and the lid rim according to a predetermined treatment method according to one of Examples 1-13.

In Example 16, a method of treating pericardial tissue including contacting at least a portion of a pericardial sac with a chemical while the pericardial sac is tensioned by an application of fluid pressure to an inside face of the pericardial sac.

In Example 17, the method of Example 16, wherein the pericardial sac is tensioned by delivering the chemical to the inside face.

In Example 18, the method of Example 16, wherein in the chemical is in an aqueous solution.

In Example 19, the method of Example 16, wherein the chemical includes glutaraldehyde.

In Example 20, the method of Example 16, further including securing a base of the pericardial sac to a rim of a pressurizing apparatus.

In Example 21, the method of Example 20, wherein the rim has a diameter within plus or minus 20% of the diameter of the base of the pericardial sac.

In Example 22, the method of Example 20, wherein the pressurizing apparatus includes at least one inlet or outlet adapted to supply at least one fluid to the inside face of the pericardial sac or evacuate a fluid from an outside face of the pericardial sac.

In Example 23, the method of Example 20, wherein the base of the pericardial sac is secured using the pressurizing apparatus. The pressurizing apparatus can include a vessel including a side wall and a bottom wall and the side wall can include a vessel rim. The pressurizing apparatus can include a lid having a lid rim adapted to mate with the vessel rim to form an enclosure, wherein the base of the pericardial sac is secured between the vessel rim and the lid rim.

In Example 24, the method of Example 16, wherein at least a portion of the pericardial sac is in contact with the chemical for at least 30 minutes.

In Example 25, the method of Example 24, wherein the fluid pressure applied to the inside face of the pericardial sac is varied during contact with the chemical.

In Example 26, the method of Example 16, wherein the inside face is pressurized to a pressure of at least 0.4 atmospheres.

In Example 27, the method of Example 16, wherein the inside face is pressurized up to a pressure of 3 atmospheres.

In Example 28, the method of Example 16, wherein the inside face is treated with a first chemical solution and an outside face is treated with a second chemical solution that is different from the first chemical solution.

In Example 29, the method of Example 16, wherein the inside face is treated with a chemical while the inside face is pressurized at a first pressure and an outside face is treated with a chemical while the inside face is pressurized at a second pressure that is different from the first pressure.

In Example 30, the method of Example 16, wherein the inside face is pressurized to a pulsed pressure, the pulsed pressure being applied to the inside face between 1 to 20 times per minute.

In Example 31, an apparatus for treating pericardial tissue including:
a vessel including a side wall and a bottom wall, the side wall including a vessel rim, the vessel having at least one vessel inlet or vessel outlet; and
a lid having a lid rim adapted to mate with the vessel rim to form an enclosure, the lid including at least one lid inlet or lid outlet,
wherein the apparatus is adapted to secure a base of a pericardial sac between the vessel rim and the lid rim and pressurize an inside face of the pericardial sac.

In Example 32, the apparatus of Example 31, further including a controller configured to supply fluids and chemicals to the at least one vessel inlet or vessel outlet and the at least one lid inlet or lid outlet to treat a pericardial sac retained between the vessel rim and the lid rim.

In Example 33, the apparatus of Example 31, further including a pressure gauge couple to one of the vessel and the lid to detect a pressure within the vessel.

In Example 34, the apparatus of Example 31, further including a locking collar coupled to the vessel rim to seal a base of a pericardial sac to the vessel rim.

In Example 35, an apparatus for treating pericardial tissue includes a vessel and a lid. The vessel can have a side wall and a bottom wall. The side wall can include a first vessel rim and a second vessel rim. The vessel can have at least one vessel inlet or vessel outlet. The lid can have a lid rim adapted to mate with the vessel rim to form an enclosure. The lid can include at least one lid inlet or lid outlet. The apparatus can be adapted to secure a base of a pericardial sac between the second vessel rim and the lid rim and deliver chemical solutions through the first vessel rim to an inside face of the pericardial sac.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
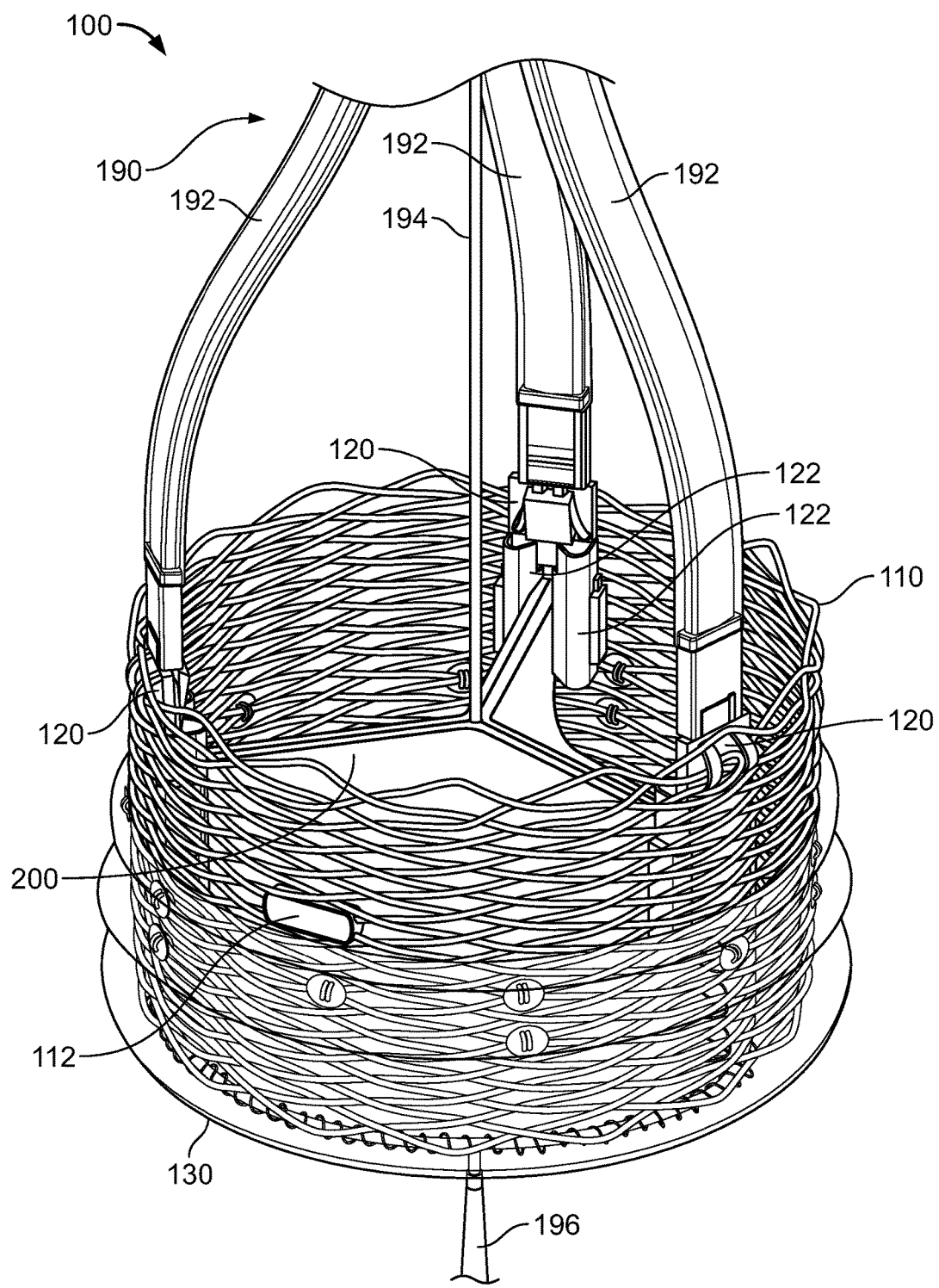
FIG. 1 is a perspective view of an exemplary prosthetic heart valve.

Methods, devices, and systems provided herein can be used to treat at least a portion of a pericardial sac for use in a medical device. For example, one or more leaflets can be cut from a treated pericardial sac and used in a prosthetic heart valve, such leaflets 200 of heart valve 100 depicted in FIG. 1. The pericardial tissue can be obtained from the pericardial sacs surrounding the hearts of animals, e.g. bovine, porcine, and equine, etc. The pericardium is a tough double layered fibroserous sac which covers the heart. The pericardium includes two layers: the outermost fibrous pericardium and the inner serous pericardium. The fibrous pericardium is made up of dense, and loose connective tissue that anchors the heart to the surrounding walls and prevents it from overfilling with blood. Pericardial tissue removed from an animal can include a layer of outermost fibrous pericardium, a layer including a least a portion of inner serous pericardium, or layers of both the outermost fibrous pericardium and the inner serous pericardium. In some cases, the pericardial sac is removed as a substantially whole pericardial sac having a concave inside surface and a convex outside surface.

Methods, devices, and systems provided herein can treat a pericardial sac with one or more chemicals while the pericardial sac is tensioned by supplying a positive fluid pressure to an inside surface of the pericardial sac. By applying a positive fluid pressure to an inside surface of the pericardial sac, the pericardial sac can balloon so that a tensile force is evenly applied to the pericardial tissue. In some cases, the chemicals can reduce the antigenicity of the pericardial tissue. In some cases, the chemicals can crosslink collagen fibers within the pericardial tissue to obtain properties desirable for a particular use, e.g., increase tissue resistance to enzymatic degradation in-vivo. Crosslinked collagen fibers can lock in mechanical properties of the pericardial tissue for the amount of tension applied using fluid pressure. For example, tissue fixed in a stretched state will have less elasticity than tissue fixed in a non-tensioned state. Moreover, tissue tensioned differently in different directions will have more elasticity in directions perpendicular to the direction of tensioning. Methods, devices, and systems provided herein, however, can apply fluid pressure to an inside surface of a pericardial sac to produce uniform tension along all axes, which can result in a more uniform elastic modulus throughout the pericardial tissue. The term "inside surface" as used herein refers to a concave surface of the pericardial sac, which refer to either side of a pericardial sac depending on the orientation of the pericardial sac during a treatment provided herein. For example, in some cases a pericardial sac treated herein can have an outside face including outermost fibrous pericardium tissue and an inside face including inner serous pericardium tissue. In some cases, a pericardial sac can be flipped inside out from its state in nature such that it has an outside face including inner serous pericardium tissue and an inside face including outermost fibrous pericardium tissue. Methods, devices, and systems provided herein can treat at least a portion of a pericardial sac by contacting at least a portion of the pericardial sac with a chemical crosslinker. In some cases, at least a portion of a pericardial sac can be treated by contacting at least a portion of the pericardial sac with a solution of glutaraldehyde. For example, a glutaraldehyde treating solution can be a buffered, aqueous solution including salts and a glutaraldehyde concentration of between 0.2% and 0.7% by weight. In some cases, the chemical crosslinker can include, for example, epoxy compounds, formaldehyde or genipin as referenced by E. Remi et. al., *Biomaterials Science and Engineering*, p. 437.

Applying fluid pressure to an inside surface of a pericardial sac can improve the tensioning of a pericardial sac during treatment as compared to techniques that cut the pericardial sac in half and tension the cut pericardial tissue in a plane during treatment. Because even cut sections of pericardial tissue is not completely flat prior to the application of tension, attempts to apply biaxial forces to the cut pericardial tissue can result in variations in an amount of tension applied in different sections of the pericardial tissue in the various directions. Moreover, pericardial tissue at the base can have an above average thickness and the apex can have a below average thickness, thus pericardial tissue at the base and apex is often discarded. Methods of treating a pericardial sac intact provided herein can allow for improved utilization of pericardial tissue. Methods, devises, and systems provided herein can tension the pericardial sac uniformly along all axes throughout the tissue during treatment to provide more uniform elastic modulus of the tissue. Additionally, methods, devices, and systems provided herein can tension and treat pericardial tissue in an orientation corresponding to its natural curved orientation (i.e. the pericardial sac's dome shape for surrounding the heart). For example, the apex can be tensioned and treated without flattening the apex using methods, devices, and systems provided herein.

Figure 2:
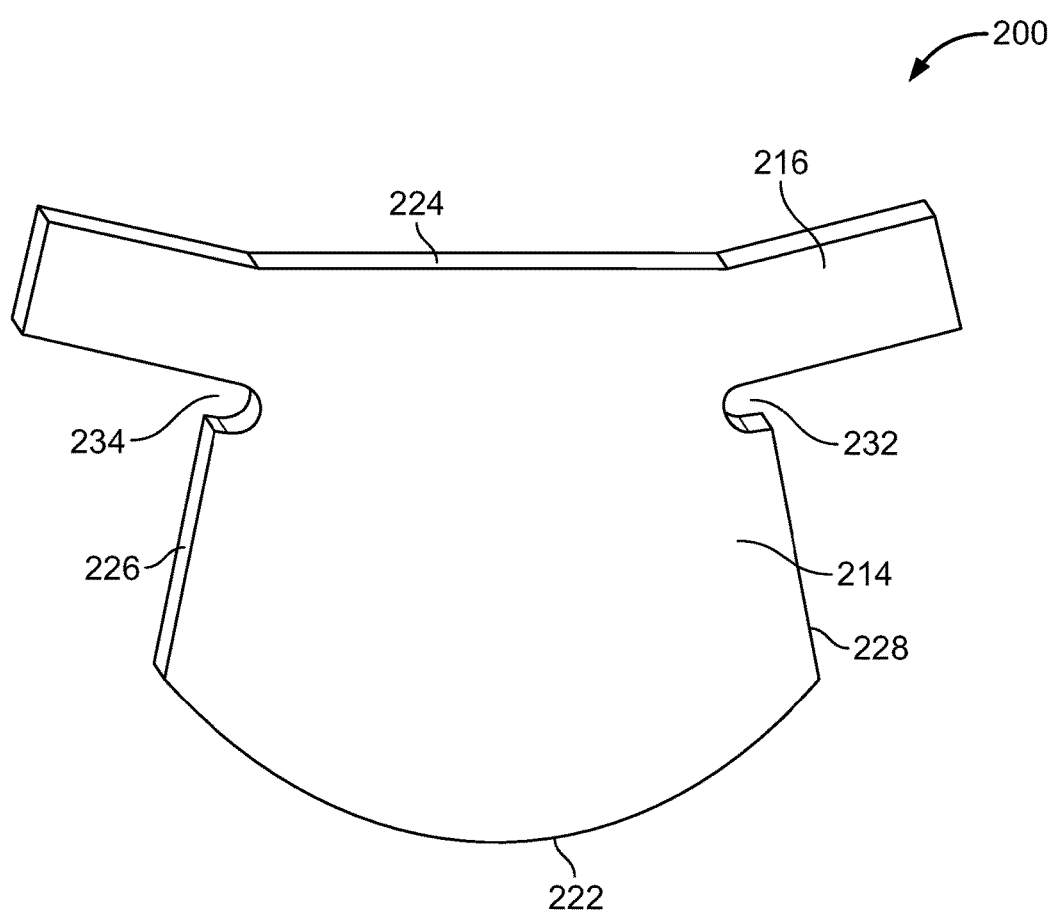
FIG. 2 is depicts an exemplary leaflet.

Methods, devices, and systems provided herein can be used to treat pericardial sacs prior to cutting the pericardial sac to form one or more predetermined shapes for use in an implantable medical device. For example, pericardial tissue treated in methods, devices, and systems provided herein can be used to form one or more leaflets, such as leaflet 200 as shown in FIG. 2 and used in exemplary prosthetic heart valve 100 depicted in FIG. 1. FIG. 1 is a perspective view of prosthetic heart valve 100 connected to a deployment device 190. As shown, prosthetic heart valve 100 includes an expandable member 110, three leaflets 200, three anchor elements 120 securing sleeve portions 216 of leaflets 200 to expandable member 110, a tubular seal 130 secured around a blood inflow end of prosthetic heart valve 100. Anchor elements 120 can include post leg structures 122 adapted to provide support along opposite sides of sleeve portions 216. Expandable member 110 can be a braided stent, which is adapted to transition between a restricted state having a smaller diameter and an expanded state having a larger diameter. Expandable member 110 can be self-expanding, mechanically expanded, or a combination thereof. Briefly, in use, prosthetic heart valve 100 can be deployed using a heart valve delivery system, which can include a sheath for retaining the prosthetic heart valve 100 with the expandable member 110 in a restricted state. Within the sheath, anchor elements 120 can be connected to pushing prongs 192 and a pull line 194 can be connected to a nose cap 196 positioned at the end of the sheath. In some cases, expandable member 110 can self-expand to a first intermediate diameter, and the system can mechanically expand expandable member 110 to a larger deployment diameter. For example, anchor elements 120 can include a locking mechanism to clip a portion of expandable member when the expandable member 110 is expanded to a predetermined locking diameter. In some cases, one or more radiopaque markers can be secured to prosthetic heart valves provided herein. For example, as shown in FIG. 1, expandable member 110 including a radiopaque marker 112. Any suitable radiopaque material (such a platinum, palladium, gold, tantalum, or alloys thereof) can be used as the radiopaque material in radiopaque marker 112. One or more radiopaque markers can be used with an imaging system to help a physician ensure that a valve is set in an appropriate location. In some cases, prosthetic heart valves provided herein include at least 3 radiopaque markers.

As shown in FIG. 1, prosthetic heart valve 100 can include a plurality of leaflets 200 including pericardial tissue treated using a method, device, or system provided herein. In some cases, such as that shown, prosthetic heart valve 100 includes three leaflets 200. In some cases, prosthetic heart valves provided herein can have any suitable number of leaflets, for example two, three, four, five, or more leaflets. In some cases, leaflets 200 are secured to one another. In some cases, leaflets 200 can be secured to one another via a plurality of sutures. Leaflets 200 can be sutured along side edges of a body portion of each leaflet. In some cases, prosthetic heart valves provide herein can include a single line of sutures, which can be adapted to minimize leaks, minimize an amount of a width of the seam, and/or minimize the profile of the replacement heart valve during percutaneous insertion. In some cases, prosthetic heart valves provide herein can include multiple lines of sutures.

Referring to FIG. 2, leaflet 200 can include pericardial tissue treated using methods, devices, and systems provided herein. As shown, leaflet 200 can include a body portion 214 and sleeve portions 216. In some cases, the body portion 214 has a bottom edge 222, a first side edge 226, a second side edge 228, and a free edge 224. Leaflet 200 further includes a front, a back, a first side adjacent to the first side edge 226, and a second side adjacent to the second side edge 228. Leaflets 200 can be assembled by aligning two leaflets 200 to position side regions of opposite leaflets 200 adjacent to each other to stitch the leaflets 200 together along a stitch line (not shown). Leaflet 200 can define notches 232 and 234 along the side edges 228 and 226 adjacent to sleeve portions 216.

Figure 3:
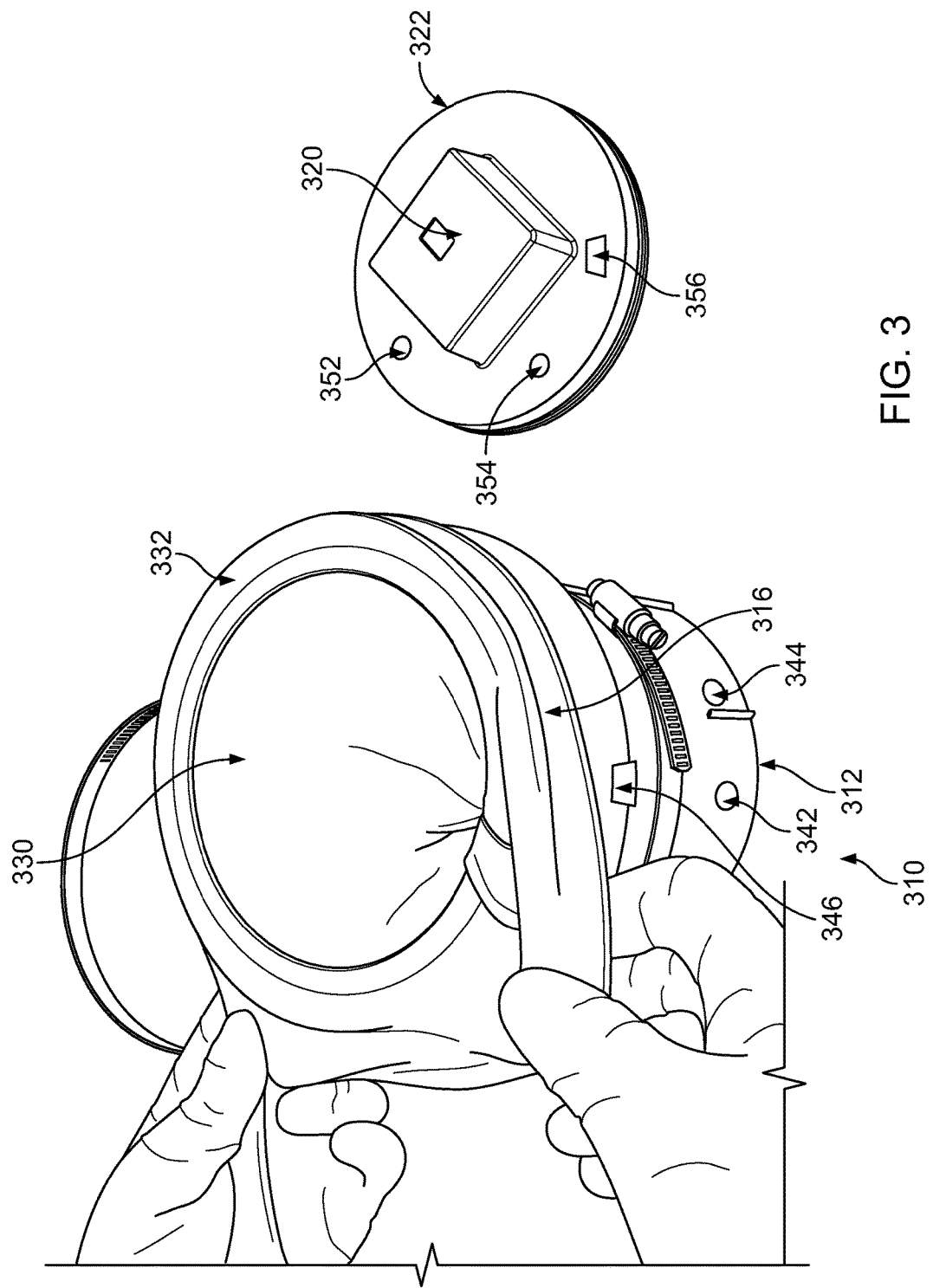
FIGS. 3, 4A, 4B and 5-8 depict the use of an exemplary pericardial sac treatment apparatus.
Figure 4A:
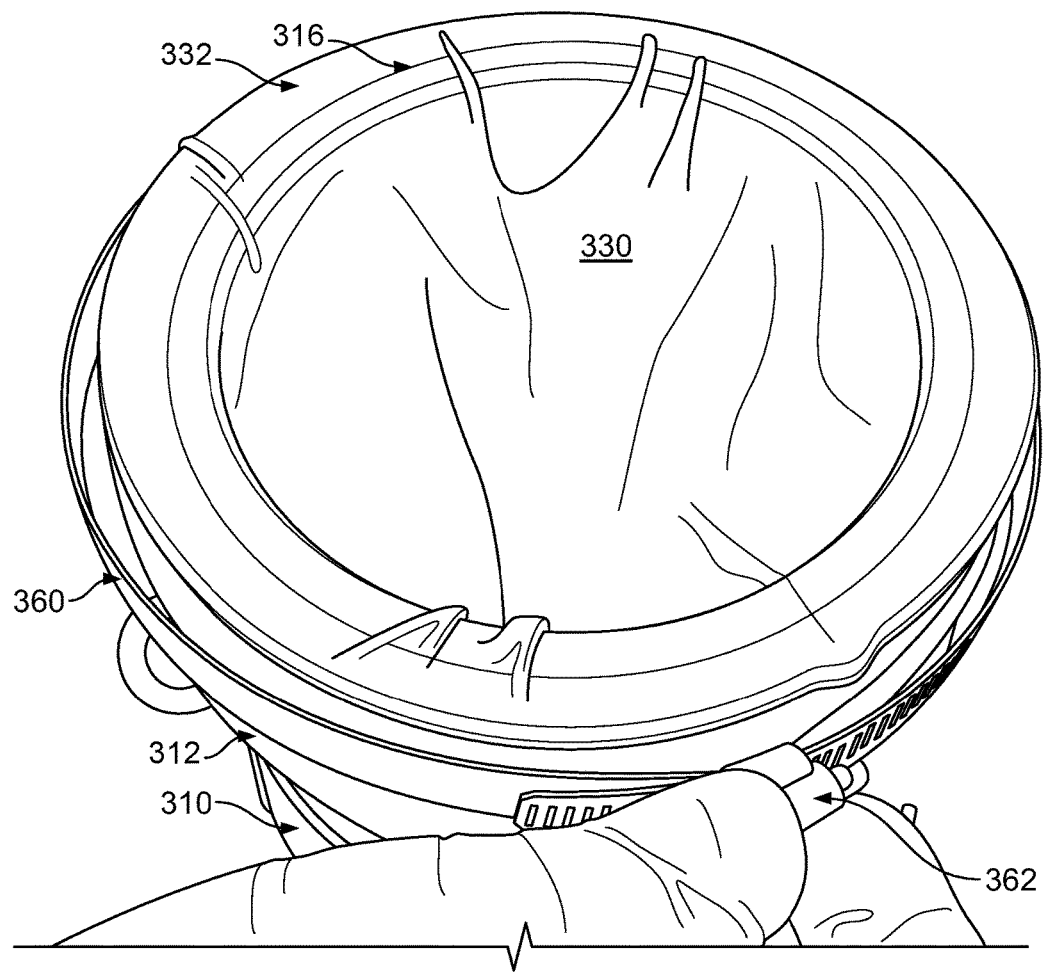
Figure 4B:
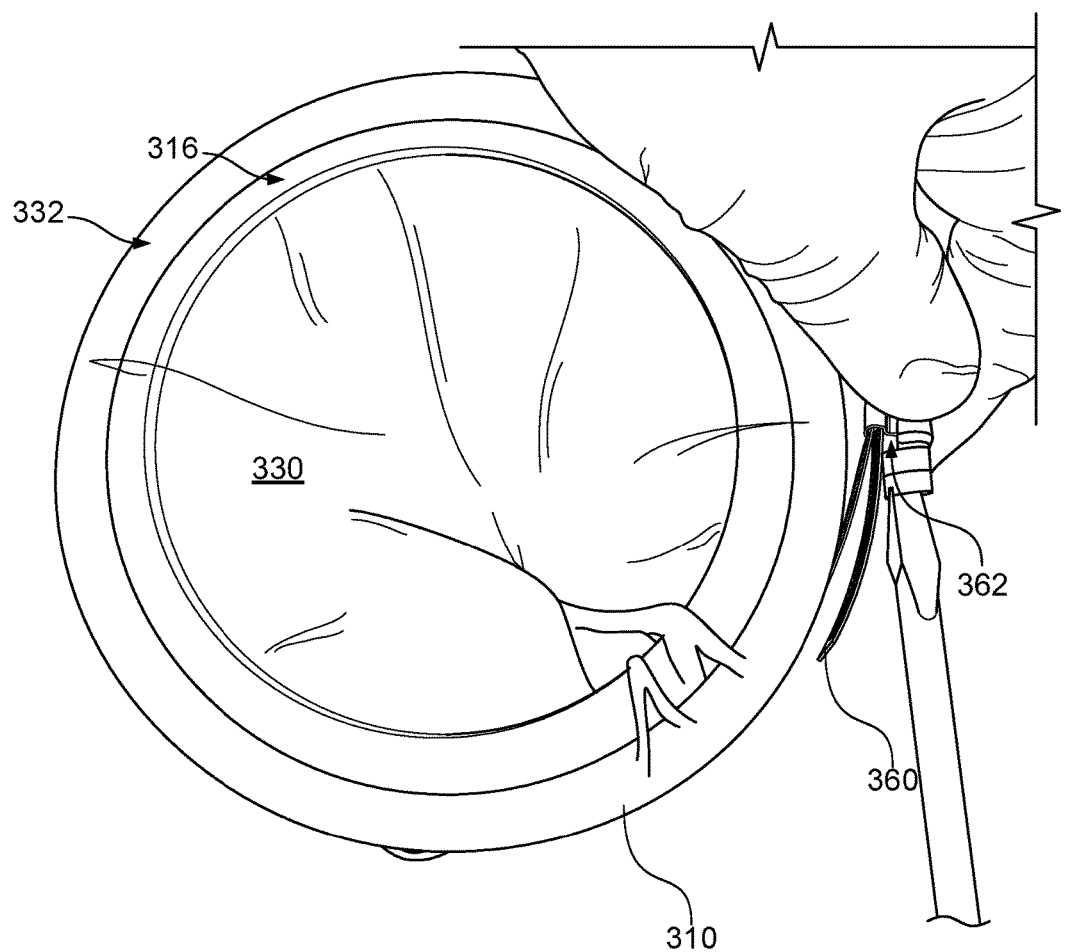

FIGS. 3-8 depict an exemplary treatment system include a vessel 310 and a lid 320 being used to treat a pericardial sac 330. Vessel 310 includes a side wall having a first vessel rim 312 and a second vessel rim 316. Lid 320 includes a lid rim 322. FIG. 3 depicts a base 332 of a pericardial sac 330 being positioned over second vessel rim 316 such that the base 332 of the pericardial sac overlies the second vessel rim 316. As shown, vessel 310 can optionally include a vessel inlet 342 and/or a vessel outlet 344. As shown, lid 320 can optionally include a lid inlet 352 and/or a lid outlet 354. Inlets 342, 352 and outlets 344, 354 can be controlled with one or more controllers to pump fluids (liquids or gasses) into or out of vessel 310 to achieve one or more desired pressures. In some cases, a pressure gauge 346, 356 can be included in the vessel or in the lid to detect a pressure within the vessel 310. FIGS. 4A and 4B show the sealing of a base 332 of a pericardial sac 330 to second vessel rim 316 using a locking collar 360. FIG. 4A is a perspective view. FIG. 4B is a top view. As shown, locking collar 360 can be tightened by turning tightening screw 362.

Figure 5:
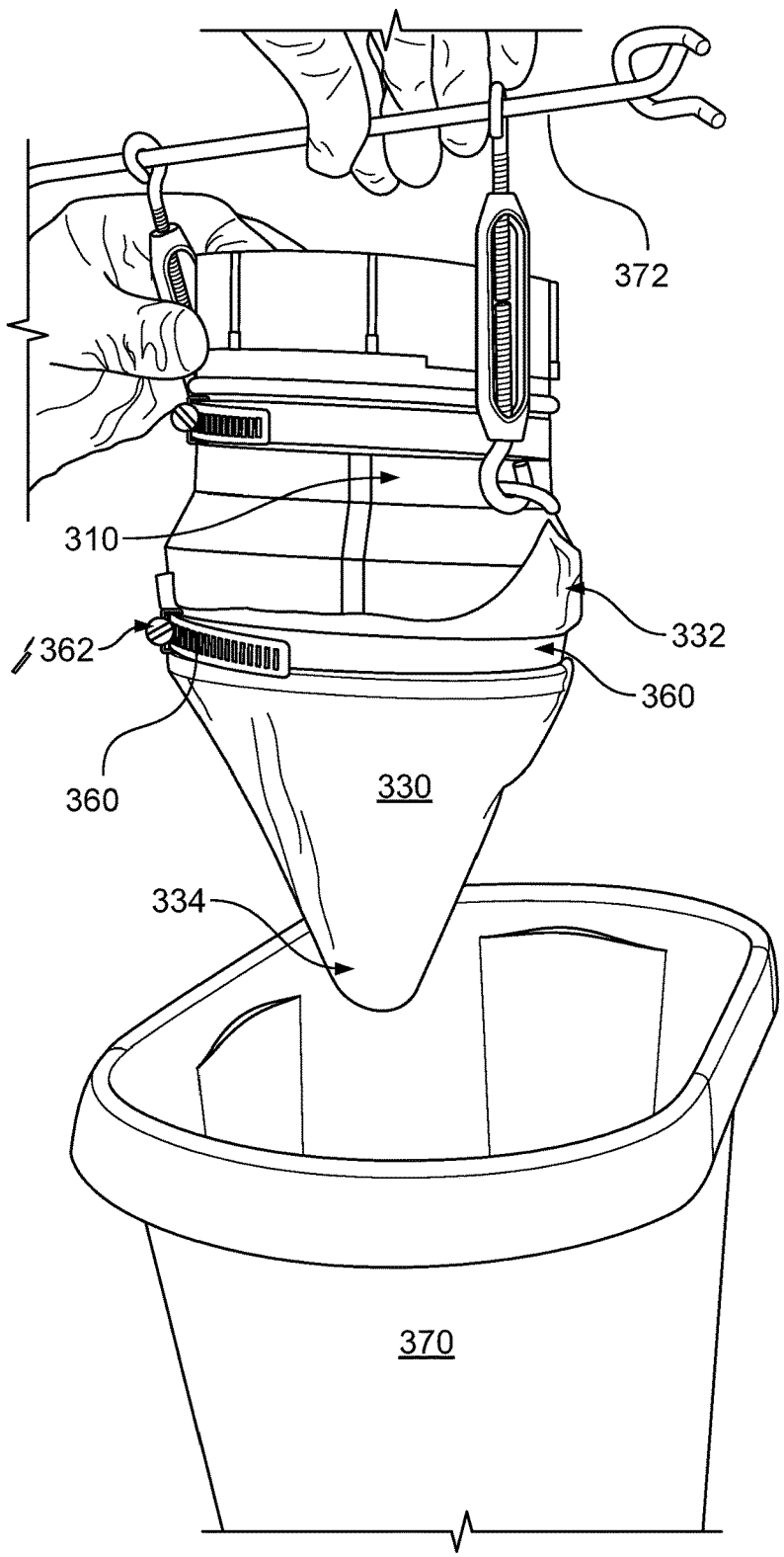
Figure 6:
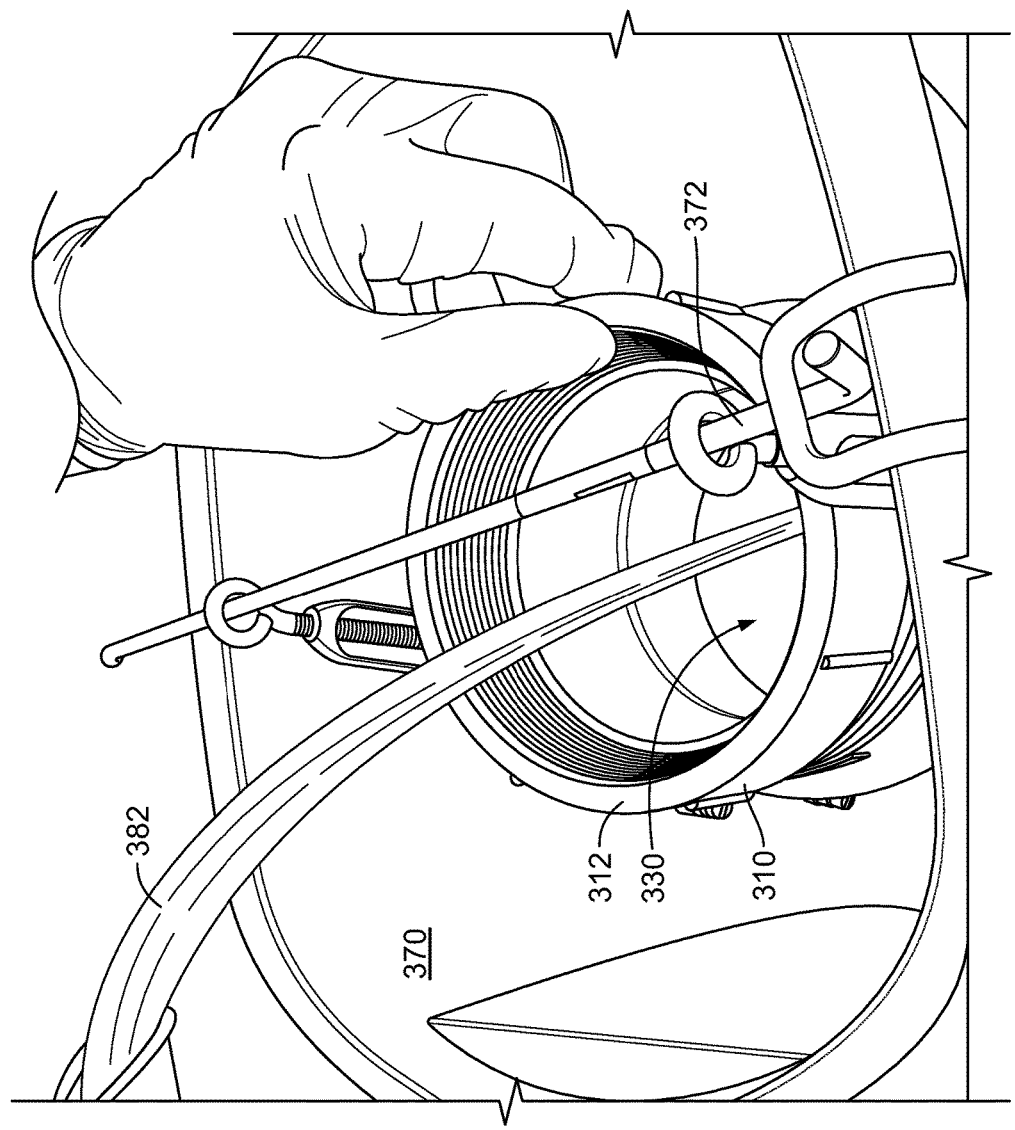
Figure 7:
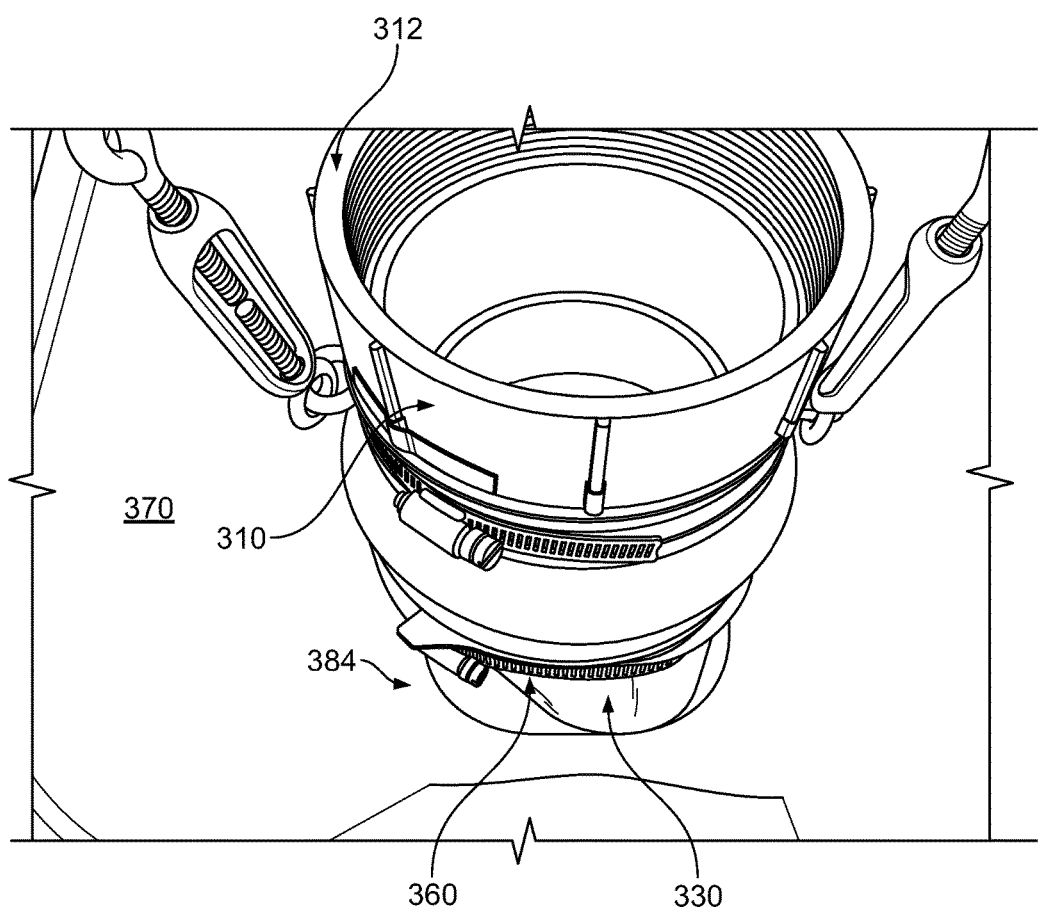
Figure 8:
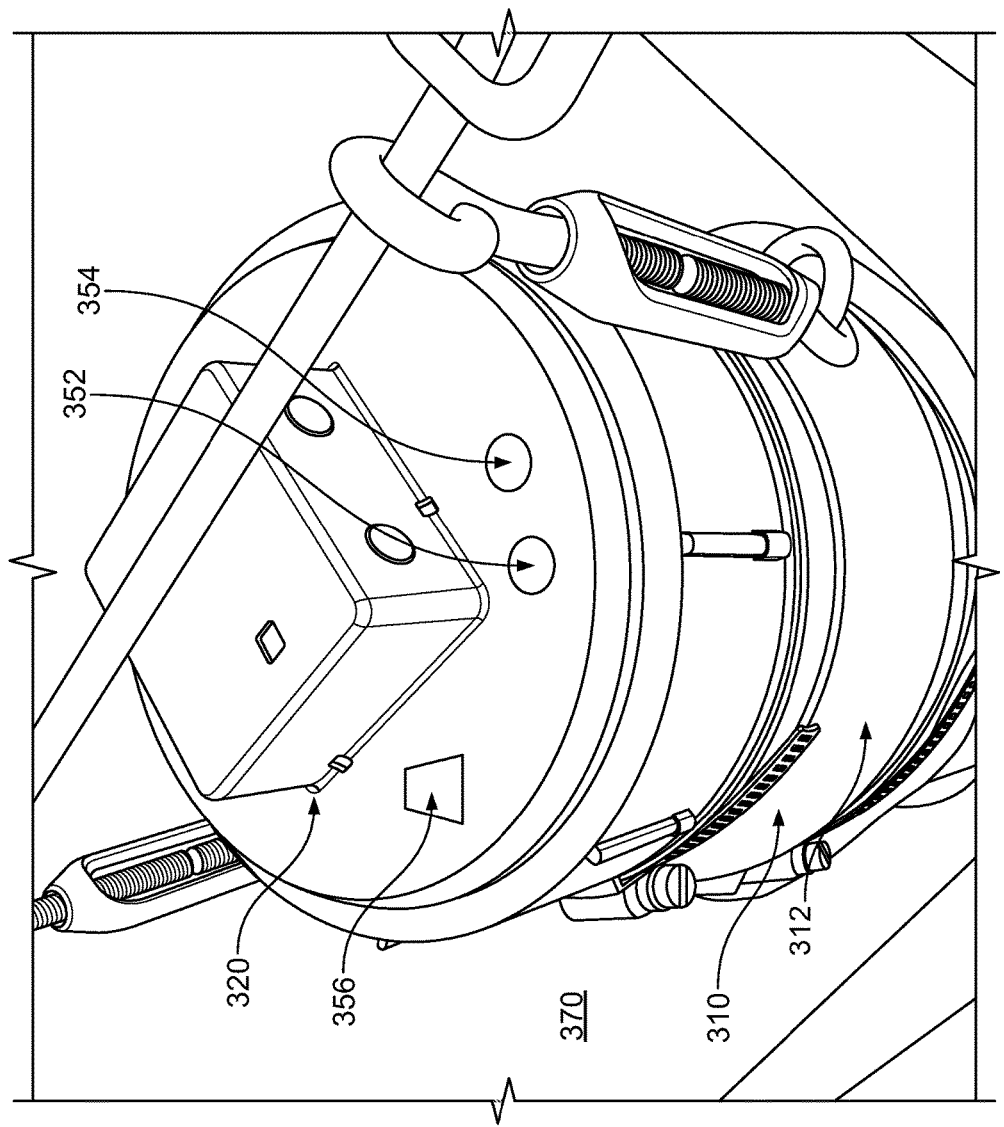

Once a pericardial sac 330 is secured to vessel 310, vessel 310 and pericardial sac 330 can be positioned with first vessel rim 312 upward for filling vessel 310 with a treatment fluid. As shown in FIG. 5, vessel 310 can be positioned in an outer treatment vessel 370 with pericardial sac 330 extending downward. Vessel 310 can be supported by a cross bar 372 extending over outer treatment vessel 370. As shown in FIG. 6, chemical solution 382 can be delivered to an inside face of pericardial sac 330 by pouring chemical solution 382 through first vessel rim 312. As shown in FIG. 7, chemical solution 384 can be contained within outer treatment vessel 370 to contact an outside face of pericardial sac 330. As shown in FIG. 8, lid 320 can be applied to first vessel rim 312. In some cases, lid 320 can be screwed onto vessel 310. Once lid 320 is applied, vessel 310 can be pressurized to apply a fluid pressure to an inside face of pericardial sac 330. In some cases, an inside face can be pressurized to a pressure of at least 30.4 kilopascals (kPa), or 0.4 atmospheres. In some cases, an inside face can be pressurized to a pressure between 10.1 kPa and 30.4 kPa (or between 0.1 and 0.3 atmospheres), between 30.4 kPa and 50.7 kPa (or between 0.3 and 0.5 atmospheres), or between 50.7 kPa and 101 kPa (or between 0.5 and 1.0 atmospheres). In some cases, an inside face can be pressurized up to about 304 kPa (or 3 atmospheres). In some cases, an inside face is pressurized to a pulsed pressure. The pulsed pressure applied to the inside face between 1 to 20 times per minute. The pressure within vessel 310 can be controlled using inlet 352, outlet 354, and/or pressure gauge 356. Inlet 352 and outlet 354 can each include valves.

Although outer treatment vessel 370 is shown as being exposed to the atmosphere, in some cases outer treatment vessel 370 can be secured to vessel 310. In some cases, a pericardial sac can be sealed between an outer treatment vessel 370 and a lid and tensioned by either applying pressure to a lid side of the sealed vessel and/or by drawing a vacuum in the outer treatment vessel 370 side of the sealed vessel. Pressurizing fluids and/or treatment solutions can be delivered and removed through one or more inlet lines and/or one or more outlet lines.

Although lid 320 and vessel 310 are depicted as being two separate parts that can be secured together, in some cases a single circular or ovular lid can be directly secured to a base of a pericardial sac and filled with fluids and/or pressurized using inlets, outlets, and valves.

In some cases, both an inside face and an outside face of pericardium 330 can be treated with chemical solutions 382 and 384 at the same time. In some cases, an inside face and an outside face of pericardium 330 can be treated at different times. In some cases, chemical solutions 382 and 384 are the same chemical solution. In some cases, chemical solutions 382 and 384 are different in either concentrations and/or constituents. In some cases, a chemical solution can be a buffered, aqueous solution including salts and a glutaraldehyde concentration of between 0.2% and 0.7% by weight. In some cases, a chemical solution can include salts and a glutaraldehyde concentration of between 0.1% and 0.3% by weight, between 0.3% and 0.5% by weight, between 0.4% and 0.6% by weight, or between 0.6% and 0.9% by weight. In some cases, inside face and outside face can be treated using different pressures within vessel 310. In some cases, inside and outside faces of pericardium 330 can be treated with chemical solutions having a pH of 7 or 7.5. In some cases, the chemical solutions can have a pH of between 5 and 8. In some cases, the faces of pericardium 330 can be treated at a temperature of about 37° C. In some cases, the faces of pericardium 330 can be treated at any temperature between 20° C. and 40° C.

In some cases, devices or systems provided herein can be provided with a controller including a computer programmed to run a sequence of pressurizing and treatment steps by supplying fluids and/or chemical solutions to an inside face and/or an outside face of a pericardial sac. In some cases, the controller can be coupled to a heating unit to control and change, if applicable, the temperature during the treatment steps.

Methods, systems, and devices provided herein can differentially treat the inside face and the outside face of a pericardial sac to produce desirable properties in pericardial tissue used in an implantable medical device, such as when used as leaflets 200 in artificial heart valve 100. By comparison, merely pericardial tissue in a chemical solution results in treatment of both sides of the pericardial tissue in the same way. By treating different sides of the pericardial sac differently, it can be possible to better mimic the properties of native valve leaflets. For example, the outflow side of native valve leaflets has different properties than the inflow side of the leaflet which means that the leaflets are extremely strong and inflexible during systole when the valve is shut but are flexible and conformable in diastole when the valve opens which maximizes the annular orifice area. By treating opposite faces of the pericardial tissue differently to impart different mechanical properties, more akin to native leaflets, artificial heart valves using treated pericardial sac material treated by methods, devices, and systems provided herein may provide better bio prosthetic valve performance.

In some cases, a pericardial sac treatment apparatus provided herein can include a circular or oval plate with a removable, locking collar that can be attached to the basal portion of an intact pericardial sac. The collar used to attach the sac to the plate creates a seal. The plate can include an inlet and outlet connector, both of which can be opened or closed with a valve. The inlet connector can be used to fill the sac with liquid solution. The outlet is used to let air escape while the sac is filling with liquid. The outlet and inlet can be closed off such that a seal is formed, thus creating a filled sac resembling a "water balloon." Thus the inside of the sac (compartment A) can be filled with liquid so that the inside face of the tissue is completely wetted. The filled sac is then submerged in a bath of liquid (compartment B) so that the filled sac is completely wetted on the outside. The plate may also house a pressure gauge which can be used to measure the pressure of the filled sac, thereby providing a means to regulate the tension of the pericardial tissue. In some cases, the plate can have a dome protrusion that is placed inside the sac, thus reducing the volume of liquid required to fill the sac.

Methods provided herein can be used to treat an inside face and outside face of a pericardial sac to have the same or different properties. For example, in some cases, both the inside face and outside face contain a glutaraldehyde solution of the same concentration. In some cases, the inside face and the outside face contact glutaraldehyde solutions of different concentration. In some cases, an inside face contacts isotonic saline or PBS buffer and an outside face contacts a glutaraldehyde solution. In some cases, an outside face contacts isotonic saline or PBS buffer and an inside face contacts a glutaraldehyde solution. In some cases, an outside face initially contacts an isotonic saline or a PBS buffer and an inside face initially contacts a glutaraldehyde solution for a period of time. After a set period of time, the solutions adjacent each face are drained and then refilled such that inside face contacts isotonic saline or a PBS buffer and outside face contacts a glutaraldehyde solution. In some cases, inside and outside faces contact glutaraldehyde solutions and/or isotonic saline or a PBS buffer as described above in this paragraph, and the fluid pressure applied to the inside face of the pericardial sac is regulated so that the tissue is at a predetermined tension. In some cases, a pressure applied to an inside face of the pericardial sac is pulsed or varied between two or more predetermined pressures. In some cases, a pressure applied to the pericardial sac can be greater or lower when contacting an inside face with a glutaraldehyde solution versus when contacting an outside face with a glutaraldehyde solution.

Once a pericardial sac (such as pericardial sac 330) is treated, parts for medical devices (such as leaflets 200) are cut from the pericardial sac. By treating pericardial sac retaining its natural curvature, more material can be used in attempting to match the pericardial sac tissue properties to the desired mechanical properties, thus methods, devices, and systems provided herein can reduce an amount of pericardial tissue wasted. In some cases, a treated pericardial sac can be secured over a dome-shaped template, such as described in WO 2012/177941 A1, which is hereby incorporated by reference. As described in WO 2012/177941 A1, the dome-shaped template can be used to reproduce the original shape of a heart when preparing tissue. A dome-shaped cutting template can include features that show biological structures to help align a treated pericardial sac to the dome-shaped cutting template for a subsequent cutting of the pericardial sac to obtain parts of a medical device, such as leaflets 200. In some cases, a second cutting template can be applied to dome-shaped cutting template to guide the direct cutting of a leaflet or other part for a medical device. Because leaflets (or other medical device parts) can be cut directly from a substantially intact pericardial sac, less material is wasted. Additionally, pericardial tissue at the apex can be harvested for applications requiring thinner pericardial tissue.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating pericardial tissue comprising:
    securing a base of a pericardial sac to a vessel, the vessel comprising a side wall having a first vessel rim and a second vessel rim;
    contacting at least a portion of the pericardial sac with a chemical while the pericardial sac is tensioned by an application of fluid pressure to an inside face of the pericardial sac;
    wherein the first vessel rim is adapted to mate with a lid to form an enclosure; and
    wherein the base of the pericardial sac is secured between the second vessel rim and a locking collar.

2. The method of claim 1, wherein the pericardial sac is tensioned by delivering the chemical to the inside face.

3. The method of claim 1, wherein in the chemical is in an aqueous solution.

4. The method of claim 1, wherein the chemical comprises glutaraldehyde.

5. The method of claim 1, wherein the second vessel rim has a diameter within plus or minus 20% of the diameter of the base of the pericardial sac.

6. The method of claim 1, wherein the vessel comprises at least one inlet or outlet adapted to supply at least one fluid to the inside face of the pericardial sac or evacuate a fluid from an outside face of the pericardial sac.

7. The method of claim 1, wherein at least a portion of the pericardial sac is in contact with the chemical for at least 30 minutes.

8. The method of claim 7, wherein the fluid pressure applied to the inside face of the pericardial sac is varied during contact with the chemical.

9. The method of claim 1, wherein the inside face is pressurized to a pressure of at least 0.4 atmospheres.

10. The method of claim 1, wherein the inside face is pressurized up to a pressure of 3 atmospheres.

11. The method of claim 1, wherein the inside face is treated with a first chemical solution and an outside face is treated with a second chemical solution that is different from the first chemical solution.

12. The method of claim 1, wherein the inside face is treated with a chemical while the inside face is pressurized at a first pressure and an outside face is treated with a chemical while the inside face is pressurized at a second pressure that is different from the first pressure.

13. The method of claim 1, wherein the inside face is pressurized to a pulsed pressure, the pulsed pressure being applied to the inside face between 1 to 20 times per minute.

14. An apparatus for treating pericardial tissue comprising:
    a vessel comprising a side wall, the side wall comprising a first vessel rim and a second vessel rim, the vessel having at least one vessel inlet or vessel outlet;
    a lid having a lid rim adapted to mate with the first vessel rim to form an enclosure, the lid comprising at least one lid inlet or lid outlet, and
    a locking collar;
    wherein the vessel is adapted to secure a base of a pericardial sac between the second vessel rim and the locking collar and to pressurize an inside face of the pericardial sac.

15. The apparatus of claim 14, further comprising a controller configured to supply fluids and chemicals to the at least one vessel inlet or outlet and the at least one lid inlet or lid outlet to treat a pericardial sac retained between the second vessel rim and the locking collar.

16. The apparatus of claim 14, further comprising a pressure gauge coupled to one of the vessel and the lid to detect a pressure within the vessel.

17. An apparatus for treating pericardial tissue comprising:
- a vessel comprising a side wall, the side wall comprising a first vessel rim and a second vessel rim, the vessel having at least one vessel inlet or vessel outlet;
- a lid having a lid rim adapted to mate with the first vessel rim to form an enclosure, the lid comprising at least one lid inlet or lid outlet, and
- a locking collar;
- wherein the vessel is adapted to secure a base of a pericardial sac between the second vessel rim and the locking collar and to deliver chemical solutions through the first vessel rim to an inside face of the pericardial sac.

* * * * *